(12) United States Patent
Cawthorne et al.

(10) Patent No.: US 7,026,289 B2
(45) Date of Patent: *Apr. 11, 2006

(54) METHOD AND COMPOSITIONS FOR TREATING HYPERLIPIDEMIA AND OTHER CONDITIONS

(75) Inventors: Michael Anthony Cawthorne, Horsham (GB); Yong-Ling Liu, Buckingham (GB); Matthew V. Sennitt, Shipstead (GB)

(73) Assignee: Societe de Conseils de Recherches et d'Applications Scientifiques, SAS, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/423,683

(22) PCT Filed: May 13, 1998

(86) PCT No.: PCT/EP98/02998

§ 371 (c)(1), (2), (4) Date: Mar. 20, 2000

(87) PCT Pub. No.: WO98/51330

PCT Pub. Date: Nov. 19, 1998

(65) Prior Publication Data
US 2002/0151500 A1 Oct. 17, 2002

Related U.S. Application Data

(63) Continuation of application No. 08/855,311, filed on May 13, 1997, now abandoned.

(51) Int. Cl.
*A61K 38/31* (2006.01)

(52) U.S. Cl. .................. 514/11; 514/12; 514/16; 530/311; 530/328

(58) Field of Classification Search ............. 514/2, 514/16; 530/311, 328
See application file for complete search history.

(56) References Cited

U.S. PATENT DOCUMENTS

| | | |
|---|---|---|
| 4,133,782 A | 1/1979 | Vale, Jr. et al. |
| 4,146,612 A | 3/1979 | Veber |
| 4,190,575 A | 2/1980 | Sarantakis |
| 4,190,648 A | 2/1980 | Veber |
| 4,209,426 A | 6/1980 | Sarantakis |
| 4,211,693 A | 7/1980 | Rivier et al. |
| 4,215,039 A | 7/1980 | Sarantakis |
| 4,224,199 A | 9/1980 | Meyers et al. |
| 4,235,886 A | 11/1980 | Freidinger et al. |
| 4,238,481 A | 12/1980 | Rink et al. |
| 4,261,885 A | 4/1981 | Sakakibara et al. |
| 4,282,143 A | 8/1981 | Sarantakis |
| 4,291,022 A | 9/1981 | Sandrin et al. |
| 4,310,518 A | 1/1982 | Freidinger et al. |
| 4,316,890 A | 2/1982 | Kamber et al. |
| 4,328,214 A | 5/1982 | Rink et al. |
| 4,358,439 A | 11/1982 | Sieber et al. |
| 4,360,516 A | 11/1982 | Freidinger et al. |
| 4,369,179 A | 1/1983 | Rink et al. |
| 4,395,403 A | 7/1983 | Bauer et al. |
| 4,435,385 A | 3/1984 | Bauer et al. |
| 4,485,101 A | 11/1984 | Coy et al. |
| 4,486,415 A | 12/1984 | Freidinger |
| 4,522,813 A | 6/1985 | Nutt |
| 4,585,755 A | 4/1986 | Morgan et al. |
| 4,603,120 A | 7/1986 | Kamber |
| 4,650,787 A | 3/1987 | Schally et al. |
| 4,684,620 A | 8/1987 | Hurby et al. |
| 4,725,577 A | 2/1988 | Schally et al. |
| 4,728,638 A | 3/1988 | Bauer et al. |
| 4,853,371 A | 8/1989 | Coy et al. |
| 4,871,717 A | 10/1989 | Coy et al. |
| 4,904,642 A | 2/1990 | Coy et al. |
| 5,506,339 A | 4/1996 | Coy et al. |
| 5,708,135 A | 1/1998 | Coy et al. .................. 530/311 |
| 5,763,200 A | 6/1998 | Dunmore et al. ............ 435/721 |
| 6,004,928 A * | 12/1999 | Cawthorne et al. ........... 514/11 |

FOREIGN PATENT DOCUMENTS

| | | |
|---|---|---|
| EP | 0 030 920 | 6/1981 |
| EP | 0 083 305 | 7/1983 |
| EP | 0 203 031 | 11/1986 |
| EP | 0 329 295 | 8/1989 |
| EP | 0 363 589 | 4/1990 |
| EP | 0 389 180 A1 | 9/1990 |

(Continued)

OTHER PUBLICATIONS

Moller et al., Clin. Science, vol. 75, pp. 345-350, 1988.*

(Continued)

*Primary Examiner*—Jon Weber
*Assistant Examiner*—Abdel A. Mohamed
(74) *Attorney, Agent, or Firm*—Fish & Richardson; Brian R. Morrill; Alan F. Feeney

(57) ABSTRACT

The present invention relates to a method of treating hyperlipidemia and to reducing triacylglycerols, glycerol and cholesterol in a patient. The method includes the step of administering a therapeutically effective amount of a type-5 selective somatostatin agonist to said patient. A pharmaceutical composition comprises said agonist and such product is used in the preparation of the composition for use in treating hyperlipidemia or reducing triacylglycerols, glycerol and cholesterol in a patient's body.

12 Claims, No Drawings

FOREIGN PATENT DOCUMENTS

| | | |
|---|---|---|
| EP | 0 395 417 | 10/1990 |
| EP | 0 505 680 | 9/1992 |
| GB | 2 095 261 | 9/1982 |
| WO | 88/02756 | 4/1988 |
| WO | 88/05052 | 7/1988 |
| WO | 90/12811 | 11/1990 |
| WO | 91/09056 | 6/1991 |
| WO | 91/18016 | 11/1991 |
| WO | WO 96/35950 | * 11/1996 |
| WO | WO9635950 | 11/1996 |
| WO | 97/01579 | 1/1997 |
| WO | WO9711962 | 4/1997 |
| WO | WO9810786 | 3/1998 |

OTHER PUBLICATIONS

Ginsberg, et al., "Effect of Somatostatin-induced Suppression of Postprndial Insulin Response upon the Hypertriglyceridemia Associated with a High Carbohydrate Diet," 1982, J. Clinical Invest. 70:1225-1233.

Pointner, H., et al., "Somatostatin Inhibits the Increase of Serum Triglyceride Concentration Following a Test Meal," 1976, Scan. J. Gastroenterology 2:51.

Bruno, J., et al., "Molecular cloning and functional expression of a brain-specific somatostatin receptor," 1992, Proc. Nat. Acad. Sci., 89:11151-11155.

Cohen, et al., "Effects of octreotide on lipid metabolism in acromegaly," 1992, Hrom. Metab. Res., 24:397-400.

Davenport, et al., "Somatostatin type 5 receptors mediate the inhibitory action of somatostatin on insulin secretion in zucker fatty rat perfused pancreas," 1995, Diabetologia, 38 (supp 01) :A106, abs. No. 410.

Fukushima, et al., "Effect of simultaneous infusion of a somatostatin analogue, insulin and glucose on serum triglycerides and blood glucose levels in man," 1985, Endocinol. Japon., 32 (2) :241-248.

Horvath, A., et al., "Conformations of somatostatin analogues having antitumor activity," 1992, Peptides, p533-534.

James, et al., "Carbohydrate tolerance and serum lipids in acromegaly before and during treatment with high dose octreotide," 1991, Diabetic Medicine, 8:517-523.

Martin, et al., "Effect of a zinc phosphate suspension of a long-acting somatostatin analog on postprandial plasma glucose, triglyceride and glucagons concentration in alloxan diabetic dogs," 1984, Life Sciences, 35:2627-2633.

Nakabayshi, et al., "Effect of somatostatin on the flow rate and triglyceride levels of thoracic duct lymph in normal and vagotomized dogs," 1981, Diabetes, 30:440-445.

Van Binst, G., et al., "Backbone modifications in somatostatin analogues: Relation between conformation and activity," 1992, Peptide Research, 5(1) :8-13.

* cited by examiner

METHOD AND COMPOSITIONS FOR TREATING HYPERLIPIDEMIA AND OTHER CONDITIONS

This is a national stage of International Patent Application No. PCT/EP98/02998, with an international filing date of May 13, 1998, now pending, which is a continuation of U.S. patent application Ser. No. 08/855,311, with a filing date of May 13, 1997, now abandoned.

This invention relates to a method and to compositions useful in the treatment of hyperlipidemia and other conditions, for example high levels of triacylglycerols, glycerol or cholesterol in a patient.

BACKGROUND OF THE INVENTION

There are substantial epidemiologic, clinical, genetic and experimental evidence that suggested a primary role of plasma lipids and lipoproteins in atherogenesis (Adult Treatment Panel II, Circulation 89:1333–1445 (1994); Havel, R. J., Clin. Exp. Hypertens. 11:887–900 (1989)). Atherogenesis is the process by which lipids accumulate in the intimal lining of arteries leading to the formation of plaques and hardening of the vessel wall or atherosclerosis. Although the exact mechanism leading to atherogenesis is still not well understood, abnormalities of lipid and lipoprotein metabolism, coagulation, hyperinsulinism and glycation all seem to contribute significantly to the process (Bierman, E. L., Arterio. Throm. 12:647–656 (1992)). Hyperlipidemia's characteristics of raised plasma concentrations of triglyceride, raised low density lipoprotein (LDL) cholesterol concentrations, and low concentrations of high density lipoprotein (HDL) cholesterol are known independent risk factors for atherosclerosis and its clinical sequelae, ischemic heart disease or coronary heart disease (Harrison's Principles of Internal Medicine, Eds. Braunwald, E., et al., 11th Edition, McGraw-Hill, 1016–1024 (1988); Reaven, G M, et al., N. Engl. J. Med. 334:374–381 (1996); and Hamsten, A., et al., N. Engl. J. Med. 313:1557–1563 (1985)). Hyperlipidemia in clinical practice, defined by the upper 10 percent of the distribution of plasma lipid levels in a population, i.e., serum cholesterol of 205 mg/dl or higher, serum triglycerides of 200 mg/dl, is usually recommended for treatment (Havel, R. J., et al., N. Engl. J. Med. 332:1491–1498 (1995)). Routine measurements of concentrations of cholesterol and triacylglycerides in the plasma have become widespread in clinical practice which permits the identification of patients with asymptomatic hyperlipidemia. Guidelines are available for diagnosis and monitoring responses to therapy. See Workshop Treatment of Hyperlipidemia, 1996-2 (Lakesmedelsverket, Uppsala, Sweden 1996). Lowering plasma lipid concentrations reduces the amount of atherogenic plaques on the intima of blood vessels (Pathologic Basis of Disease, Eds. S. L. Robbins, et al., 3rd Edition, W. B. Saunders 506–518 (1984); Levine, G. N., et al., N. Engl. J. Med. 332:512–521 (1995)).

A number of disorders are associated with hyperlipidemia, such as uncontrolled diabetes mellitus (insulin-dependent diabetes mellitus and non-insulin-dependent diabetes mellitus) (Bianchi, R., et al., Diab. Nutr. Metabl. 7:43–51 (1994); Welborn, T. A., Aust. N Z J. Med. 24:61–64 (1994)), hypothyroidism, uremia, nephrotic syndrome, acromegaly, obstructive liver disease, dysproteinemia (multiple myeloma, lupus erythematosus) (Harrison's Principles of Internal Medicine, Ed. Braunwald, E., et al., 11th Edition, McGraw-Hill 1016–1024 (1988)). A number of drugs also produce hyperlipidemia, such as oral contraceptives, estrogens, glucocorticoids and antihypertensives. Dietary factors such as increased caloric intake (recent weight gain), consumption of foods high in saturated fats and cholesterol and alcohol intake contribute to the development of hyperlipidemia. Aside from these, primary hyperlipidemia include a family of genetic disorders associated with family histories of hyperlipidemia or xanthomas and pancreatitis.

The administration of somatostatin has been shown to reduce plasma triglyceride concentrations in alloxan diabetic dogs (Martin, C., et al., Life Sci. 35:2627–2633 (1984)), normal humans (Moller, N., et al., Clin. Sci., 75:345–350 (1988); Fukushima, H., et al., Endocrinol. Japan., 32:241–248 (1985)) and acromegalics (Cohen, R., et al., Horm. Metab. Res., 24:397–400 (1992); James, R. A., et al., Diabet. Med. 8:517 (1991). Five distinct somatostatin receptor subtypes have been isolated. While the somatostatin type-5 receptor has been found in various areas of the brain, it has not been found in the major tissues associated with lipid metabolism, such as the liver, pancreas, and muscle. See, Bruno, et al., Endocrinology 133:2561 (1993). The present invention relates to the discovery that the somatostatin type-5 receptor is responsible for this reduction of plasma lipids.

SUMMARY OF THE INVENTION

The present invention relates to a method of treating hyperlipidemia in a patient (e.g., a mammal such as a human). The method includes the step of administering a therapeutically effective amount of a somatostatin type-5 receptor (SSTR-5) agonist (e.g., a somatostatin type-5 selective agonist) to said patient. The present invention also relates to a method of lowering the amount of cholesterol (e.g., total cholesterol or LDL cholesterol), triacylglycerols (e.g, triglycerides), or glycerol in a patient. The method includes the step of administering a therapeutically effective amount of a somatostatin type-5 receptor (SSTR-5) agonist to said patient (e.g., a somatostatin type-5 receptor selective agonist). The somatostatin agonist may be administered parenterally, e.g., administered intravenously, subcutaneously, or by implantation of a sustained release formulation. In one embodiment, the patient is suffering from hyperlipidemia (e.g., abnormally high levels of cholesterol, triacylglycerols, or glycerol) and/or is a diabetic (i.e., type-I or type-II diabetic).

The invention also provides a pharmaceutical composition comprising a therapeutically effective amount of a somatostatin type-5 receptor, optionally selective, agonist. The invention also provides the use of such agonist in the preparation of such composition for the treatment of hyperlipidemia and/or reduction in levels of triacylglycerols, glycerol or cholesterol in a human or mammalian animal.

Definitions of "somatostatin type-5 receptor agonist" and "somatostatin type-5 receptor selective agonist" will be given below. A therapeutically effective amount depends upon the condition being treated, the route of administration chosen, and the specific activity of the compound used and ultimately will be decided by the attending physician or veterinarian (e.g., between 5:g/day and 5 mg/day). In one embodiment, the somatostatin agonist is administered to the patient until the patient's lipid levels (e.g., glycerol, triacylglycerols, or cholesterol) decrease. In another embodiment, the somatostatin agonist is administered for the lifetime of the patient.

The somatostatin agonist may be injected parenterally, e.g., intravenously, into the bloodstream of the subject being treated. However, it will be readily appreciated by those skilled in the art that the route, such as intravenous, subcutaneous, intramuscular, intraperitoneal, enterally, transdermally, transmucously, sustained released polymer compositions (e.g., a lactic acid polymer or lactic acid and glycolic acid copolymer microparticle or implant), profusion, nasal, oral, etc., will vary with the condition being treated and the activity and bioavailability of the somatostatin agonist being used.

While it is possible for the somatostatin agonist to be administered as the pure or substantially pure compound, it may also be presented as a pharmaceutical formulation or preparation. The formulations to be used in the present invention, for both humans and animals, comprise any of the somatostatin agonists to be described below, together with one or more pharmaceutically acceptable carriers thereof, and optionally other therapeutic ingredients.

The carrier must be "acceptable" in the sense of being compatible with the active ingredient(s) of the formulation (e.g., capable of stabilizing peptides) and not deleterious to the subject to be treated. Desirably, the formulation should not include oxidizing agents or other substances with which peptides are known to be incompatible. For example, somatostatin agonists in the cyclized form (e.g., internal cysteine disulfide bond) can be oxidized; thus, the presence of reducing agents as excipients could lead to an opening of the cysteine disulfide bridge. On the other hand, highly oxidative conditions can lead to the formation of cysteine sulfoxide and to the oxidation of tryptophane. Consequently, it is important to carefully select the excipient. pH is another key factor, and it may be necessary to buffer the product under slightly acidic conditions (pH 5 to 6).

The formulations may conveniently be presented in unit dosage form and may be prepared by any of the methods well known in the art of pharmacy. All methods include the step of bringing the active ingredient(s) into association with the carrier which constitutes one or more accessory ingredients.

In general, the formulations for tablets or powders are prepared by uniformly and intimately blending the active ingredient with finely divided solid carriers, and then, if necessary, as in the case of tablets, forming the product into the desired shape and size.

Formulations suitable for parenteral (e.g., intravenous) administration, on the other hand, conveniently comprise sterile aqueous solutions of the active ingredient(s). Preferably, the solutions are isotonic with the blood of the subject to be treated. Such formulations may be conveniently prepared by dissolving solid active ingredient(s) in water to produce an aqueous solution, and rendering said solution sterile. The formulation may be presented in unit or multi-dose containers, for example, sealed ampoules or vials.

Formulations suitable for sustained release parenteral administrations (e.g., biodegradable polymer formulations such as polyesters containing lactic or glycolic acid residues) are also well known in the art. See, e.g., U.S. Pat. Nos. 3,773,919 and 4,767,628 and PCT Publication No. WO 94/15587.

The somatostatin or somatostatin agonist may also be administered with another compound capable of lowering blood levels of triglycerides, cholesterol, or glycerol, such as fibrates (e.g., bezafibrate, gemfibrozil, and clofibrate), HMG-COA reductase inhibitors (e.g., pravastatin, simvastatin, and fluorastatin, Atorvastatin, and Lovastatin), bile cid binding resins (e.g., cholestyramine and colestipol), nicotinic acid compounds (e.g., nicotinic acid and niceritrol), and fish oils. See Workshop Treatment of Hyperlipidemia 1996-2 (Lakemedelsverket, Uppsala, Sweden, 1996).

Other features and advantages of the invention will be apparent from the following description of the preferred embodiments and from the claims.

DETAILED DESCRIPTION OF THE INVENTION

It is believed that one skilled in the art can, based on the description herein, utilize the present invention to its fullest extent. The following specific embodiments are, therefore, to be construed as merely illustrative, and not limitative of the remainder of the disclosure in any way whatsoever.

Unless defined otherwise, all technical and scientific terms used herein have the same meaning as commonly understood by one of ordinary skill in the art to which this invention belongs. Also, all publications, patent applications, patents, and other references mentioned herein are incorporated by reference.

Somatostatin and its Agonists

Somatostatin (somatotropin release inhibiting factor or SRIF) has both a 14 amino acid isoform (somatostatin-14) and a 28 amino acid isoform (somatostatin-28). See Wilson, J. & Foster, D., *Williams Textbook of Endocrinology*, p. 510 (7th ed., 1985). The compound is an inhibitor of secretion of the growth hormone and was originally isolated from the hypothalamus. Brazeau, et al., Science 179:77 (1973). Native somatostatin has a very short duration of effect in vivo since it is rapidly inactivated by endo- and exopeptidase. Many novel analogs (e.g., peptide and non-peptide compounds) have been prepared in order to enhance the duration of effect, biological activity, and selectivity (e.g., for the particular somatostatin receptor) of this hormone. Such analogs of somatostatin will be called "somatostatin agonists" herein.

Various somatostatin receptors (SSTRs) have been isolated, e.g., SSTR-1, SSTR-2, SSTR-3, SSTR-4, and SSTR-5. Thus, the somatostatin agonist may be a SSTR-1 agonist, SSTR-2 agonist, SSTR-3 agonist, SSTR-4 agonist of a SSTR-5 agonist. What is meant by a somatostatin type-5 receptor agonist (i.e., SSTR-5 agonist) is a compound which (1) has a high binding affinity (e.g., Ki of less than 5 nM or preferably less than 2 nm or less than 1 nM) for SSTR-5 (e.g., as defined by the receptor binding assay described below) and (2) decreases lipid levels (e.g., cholesterol, glycerols, or triacylglycerols) in a patient (e.g., as shown by the biological assay described below). What is meant by a somatostatin type-5 receptor selective agonist is a somatostatin agonist which (1) has a higher binding affinity (i.e., Ki) for SSTR-5 than for either SSTR-1, SSTR-2, SSTR-3, or SSTR-4 and (2) decreases lipid levels (e.g., cholesterol, glycerols, or triacylglycerols) in a patient (e.g., as shown by the biological assay described below). In one embodiment, the SSTR-5 selective agonist has a Ki for SSTR-5 that is at least 2 times (e.g., at least 5 times or at least 10 times) less than its Ki for the SSTR-2 receptor (e.g., as defined by the receptor binding assay described below). In one embodiment, the somatostatin type-5 receptor selective agonist is also a SSTR-5 agonist.

Examples of somatostatin agonists are those covered by formulae or those specifically recited in the publications set forth below, all of which are hereby incorporated by reference.

EP Application No. P5 164 EU (Inventor: G. Keri);

Van Binst, G. et al. Peptide Research 5:8 (1992);

Horvath, A. et al. Abstract, "Conformations of Somatostatin Analogs Having Antitumor Activity", 22nd European peptide Symposium, Sep. 13–19, 1992, Interlaken, Switzerland;
PCT Application No. WO 91/09056 (1991);
EP Application No. 0 363 589 A2 (1990);
U.S. Pat. No. 4,904,642 (1990);
U.S. Pat. No. 4,871,717 (1989);
U.S. Pat. No. 4,853,371 (1989);

Examples of SSTR-5 selective somatostatin agonists include, but are not limited to, the following somatostatin analogs which are disclosed in the above-cited references:

| | |
|---|---|
| H-Cys-Phe-Phe-D-Trp-Lys-Thr-Phe-Cys-NH$_2$ | (BIM-23268); |
| H-D-Phe-Phe-Phe-D-Trp-Lys-Thr-Phe-Thr-NH$_2$ | (BIM-23052); |
| H-Cys-Phe-Phe-D-Trp-Lys-Ser-Phe-Cys-NH$_2$ | (BIM-23284); |
| H-Cys-Phe-Tyr-D-Trp-Lys-Thr-Phe-Cys-NH$_2$ | (BIM-23295); |
| H-Cys-Phe-Tyr(I)-D-Trp-Lys-Thr-Phe-Cys-NH$_2$ | (BIM-23313); |

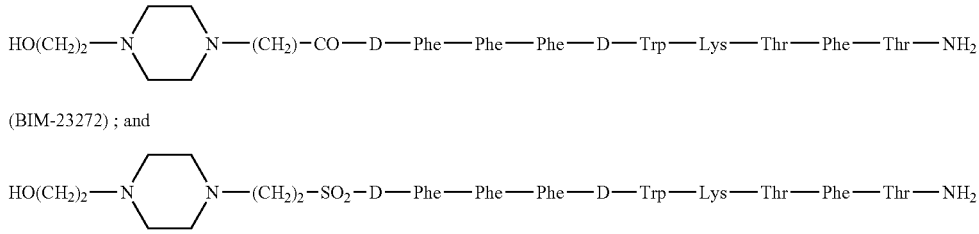

(BIM-23272); and

HO(CH$_2$)$_2$—N(piperazine)N—(CH$_2$)$_2$—SO$_2$—D—Phe—Phe—Phe—D—Trp—Lys—Thr—Phe—Thr—NH$_2$ U.S. Pat. No. 4,725,577 (1988);
U.S. Pat. No. 4,684,620 (1987);
U.S. Pat. No. 4,650,787 (1987);
U.S. Pat. No. 4,603,120 (1986);
U.S. Pat. No. 4,585,755 (1986);
EP Application No. 0 203 031 A2 (1986);
U.S. Pat. No. 4,522,813 (1985);
U.S. Pat. No. 4,486,415 (1984);
U.S. Pat. No. 4,485,101 (1984);
U.S. Pat. No. 4,435,385 (1984);
U.S. Pat. No. 4,395,403 (1983);
U.S. Pat. No. 4,369,179 (1983);
U.S. Pat. No. 4,360,516 (1982);
U.S. Pat. No. 4,358,439 (1982);
U.S. Pat. No. 4,328,214 (1982);
U.S. Pat. No. 4,316,890 (1982);
U.S. Pat. No. 4,310,518 (1982);
U.S. Pat. No. 4,291,022 (1981);
U.S. Pat. No. 4,238,481 (1980);
U.S. Pat. No. 4,235,886 (1980);
U.S. Pat. No. 4,224,199 (1980);
U.S. Pat. No. 4,211,693 (1980);
U.S. Pat. No. 4,190,648 (1980);
U.S. Pat. No. 4,146,612 (1979);
U.S. Pat. No. 4,133,782 (1979);
U.S. Pat. No. 5,506,339 (1996);
U.S. Pat. No. 4,261,885 (1981);
U.S. Pat. No. 4,728,638 (1988);
U.S. Pat. No. 4,282,143 (1981);
U.S. Pat. No. 4,215,039 (1980);
U.S. Pat. No. 4,209,426 (1980);
U.S. Pat. No. 4,190,575 (1980);
EP Patent No. 0 389 180 (1990);
EP Application No. 0 505 680 (1982);
EP Application No. 0 083 305 (1982);
EP Application No. 0 030 920 (1980);
PCT Application No. WO 88/05052 (1988);
PCT Application No. WO 90/12811 (1990);
PCT Application No. WO 97/01579 (1997);
PCT Application No. WO 91/18016 (1991);
U.K. Application No. GB 2,095,261 (1981); and
French Application No. FR 2,522,655 (1983).

Note that for all somatostatin agonists described herein, each amino acid residue represents the structure of —NH—C(R)H—CO—, in which R is the side chain (e.g., CH$_3$ for Ala). Lines between amino acid residues represent peptide bonds which join the amino acids. Also, where the amino acid residue is optically active, it is the L-form configuration that is intended unless D-form is expressly designated. A disulfide bond (e.g., a disulfide bridge) exists between the two free thiols of the Cys residues; however, it is not shown.

Synthesis of Somatostatin Agonists

The methods for synthesizing somatostatin agonists is well documented and are within the ability of a person of ordinary skill in the art.

Synthesis of short amino acid sequences is well established in the peptide art. For example, synthesis of H-D-Phe-Phe-Phe-D-Trp-Lys-Thr-Phe-Thr-NH$_2$, described above, can be achieved by following the protocol set forth in Example I of European Patent Application 0 395 417 A1. The synthesis of somatostatin agonists with a substituted N-terminus can be achieved, for example, by following the protocol set forth in WO 88/02756, European Patent Application No. 0 329 295, and PCT Publication No. WO 94/04752.

Somatostatin Receptor Binding Assays

The human SSTR-1, SSTR-2, SSTR-3, SSTR-4, and SSTR-5 cDNA clones have been described (SSTR-1 and SSTR-2 in Yamada, Y., et al., Proc. Natl. Acad. Sci. USA., 89:251–255 (1992); SSTR-3 in Yamada, et al., Mol. Endocrinol. 6:2136–2142 (1993); and SSTR-4 and SSTR-5 in Yamada, et al., Biochem. Biophys. Res. Commun. 195: 844–852 (1993)) and are also available from American Type Culture Collection (ATCC, Rockville, Md.) (ATCC Nos. 79044 (SSTR-1), 79046 (SSTR-2), and 79048 (SSTR-3)). Based on the restriction endonuclease maps, the entire coding region of each SSTR cDNA may be excised by suitable restriction endonuclease digestion (Maniatis, T., et al., *Molecular Cloning—A Laboratory Manual*, CSHL, 1982). Restriction endonucleases are available from New England Biolabs (Beverly, Mass.). This cDNA fragment was inserted into the mammalian expression vector, pCMV (Russell, D., et al., J. Biol. Chem., 264:8222–8229 (1989)), using standard molecular biology techniques (see e.g., Maniatis, T., et al., Molecular Cloning,—A Laboratory Manual, Cold Spring Harbor Laboratory, 1982) to produce the expression plasmid, pCMV-human SSTR-1 through pCMV-human SSTR-5. Other mammalian expression vectors include pcDNA1/Amp (Invitrogen, Sandlesy, Calif.). The expression plasmids were introduced into the suitable bacterial host, E. Coli HB101 (Stratagene, La Jolla, Calif.) and plasmid DNAs, for transfection, were prepared on Cesium Chloride gradients.

CHO-K1 (ovary, Chinese hamster) cells were obtained from ATCC (ATCC No. CCL 61). The cells were grown and maintained in Ham's F12 media (Gibco BRL, Grand Island, N.Y.) supplemented with 10% fetal bovine serum under standard tissue culture conditions. For transfection, the cells were seeded at a density $1\times10^6$/60-cm plate (Baxter Scientific Products, McGraw Park, Ill.). DNA mediated transfection was carried out using the calcium phosphate co-precipitation method (Ausubel, F. M., et al., Current Protocols in Molecular Biology, John Wiley & Sons, 1987). The plasmid pRSV-neo (ATCC; ATCC No. 37198) was included as a selectable marker at $\frac{1}{10}$ the concentration of the expression plasmid. CHO-K1 clonal cell lines that have stably inherited the transfected DNA were selected for growth in Ham's F12 media containing 10% fetal bovine serum and 0.5 mg/ml of G418 (Sigma). The cells were ring-cloned and expanded in the same media for analysis.

Expression of the human SSTR-1 through SSTR-5 receptors in the CHO-K1 cells were detected by Northern blot analysis of total RNA prepared from the cells (Sambrook, J. E., et al., Molecular Cloning—A Laboratory Manual, Ed. 2., Cold Spring Harbor Laboratory, Cold Spring Harbor, N.Y., 1989) and by receptor binding using [$^{125}$I-Tyr$^{11}$] somatostatin-14 as a ligand. Transfected cell lines expressing the human SSTR receptors were clonally expanded in culture and used in the following SSTR binding protocol.

Crude membranes were prepared by homogenization of the transfected cells in 20 ml of ice-cold 50 mM Tris-HCl with a POLYTRON homogenizer (setting 6, 15 sec). Buffer was added to obtain a final volume of 40 ml, and the homogenate was centrifuged in a Sorval SS-34 rotor at 39,000 g for 10 min at 0–4° C. The resulting supernatant was decanted and discarded. The pellet was rehomogenized in ice-cold buffer, diluted, and centrifuged as before. The final pellet was resuspended in the 10 mM Tris HCl and held on ice for the receptor binding assay.

Aliquots of the membrane preparation were incubated for 30 min at 30° C. with 0.05 nM [$^{125}$I-Tyr$^{11}$] somatostatin-14 (2000 Ci/mmol; Amersham Corp., Arlington Heights, Ill.) in 50 mM HEPES (pH 7.4) containing a test somatostatin agonist of various concentrations (e.g., $10^{-11}$ to $10^{-6}$), 10 mg/ml bovine serum albumin (fraction V) (Sigma Chemical Co., St. Louis, Mo.), MgCl$_2$ (5 mM), Trasylol (200 KIU ml), bacitracin (0.02 mg/ml), and phenylmethylsulphonyl fluoride (0.02 mg/ml). The final assay volume was 0.3 ml. The incubations were terminated by rapid filtration through GF/C filters (pre-soaked in 0.3% polyethylenimine for 30 min) using a Brandel filtration manifold. Each tube and filter were then washed three times with 5 ml aliquots of ice-cold buffer. Specific binding was defined as the total [$^{125}$I-Tyr$^{11}$] SRIF-14 bound minus that bound in the presence of 1000 nM. The Ki values for the tested somatostatin agonists were calculated by using the following formula: $Ki=IC_{50}/[1+(LC/LEC)]$ where $IC_{50}$ is the concentration of test somatostatin agonist required to inhibit 50 percent of the specific binding of the radioligand [$^{125}$I-Tyr$^{11}$] somatostatin-14, LC is the concentration of the radioligand (0.05 nM), and LEC is the equilibrium dissociation constant of the radioligand (0.16 nM). The Ki values (nm) for the tested somatostatin agonists are shown in Table I.

TABLE I

|  | hSSTR-1 | hSSTR-2 | hSSTR-3 | hSSTR-4 | hSSTR-5 |
|---|---|---|---|---|---|
| Somatostatin-14 | 2.26 | 0.23 | 1.2 | 1.8 | 1.41 |
| Somatostatin-28 | 2.38 | 0.30 | 1.3 | 7.93 | 0.4 |
| BIM-23268 | 1227 | 15.06 | 545 | 3551 | 0.42 |
| BIM-23052 | 97.6 | 11.96 | 5.6 | 127 | 1.22 |
| BIM-23272 | 47.7 | 3.23 | 10.9 | 753 | 1.01 |
| BIM-23284 | 27.9 | 19.3 | 35.6 | 58.6 | 0.85 |
| BIM-23295 | 86.9 | 6.19 | 9.7 | 3.4 | 0.34 |
| BIM-23313 | 151 | 4.78 | 25.5 | 55.3 | 0.30 |

Reduction of Glycerol and Triglycerides

The obese (fa/fa) Zucker and its derivative in the Zucker diabetic fatty (ZDF/Drt-fa) are excellent models of diabetes-induced dyspilidemia (Shafrir, E., Diabetes/Metabolism Rev. 8:179–208 (1992); Peterson, R. G., et al., ILAR News 32:16–19 (1990)). The animals develop progressive hyper-triglyceridemia and hypercholesterolemia.

The effect of chronic treatment with BIM-23268 on plasma lipids was examined in an obese animal model, the fatty (fa/fa) Zucker rats (Bray, G., Federation Proceedings 36:q48–153 (1977)) (purchased from Harlan-Olac, Bicester, Oxon, U.K.). Eleven male fatty Zucker rats weighing about 450 grams were randomly divided into 2 groups and their initial body wights recorded. The animals were housed in pairs in a normal 12 hour light/dark cycle at 20–21 C and fed a standard laboratory rat diet (Beekay rat and mouse diet, Bantin & Kingman, Hull, Humberside, U.K.) overnight ad libitum.

For the group assigned to receive drug treatment, the rats received BIM-23268C at 3 mg/kg, by subcutaneous injection twice a day at 10:00 a.m. and 5:00 p.m. The other group was treated with a subcutaneous injection of 0.1 ml/100 g of saline twice a day at 10:00 a.m. and 5:00 p.m. The animals were subjected to the BIM-23268 or saline treatment for a total of six days.

On the last day of treatment (day 6), food was removed at 5:00 p.m. and the rats fasted overnight. At 9:00 a.m. the next day, the animals were subjected to a glucose challenge, given as a 0.8 gram/kg of glucose orally. Periodic 400 ul of blood samples were taken from the tail vein (Peterson, R. G., ILAR News 32:16–19 (1990)) at 60 min. and 30 min. before, and at 30, 60, 90, and 120 min. after the administration of the glucose challenge (08. gram/kg orally). Aprotinin (Traysylol, Bayer UK, Hayward's Heath, W. Sussex, U.K.) and heparin (Sigma Chemical Co., Poole, Dorset, U.K.) were added to the blood samples to a final concentration of 400 KIU/ml and 100 units/ml, respectively. Plasma fractions were prepared from these samples by centrifugation at 400×G in a microfuge, for the estimation of triglycerides and glycerol. Samples were then stored at –80° C. until assayed.

Plasma glycerol and triglycerides were determined using the Sigma Enzymatic (Tinder) calorimetric assay kit (Cat #337-B, Sigma Chemical Co., Poole, Dorset, U.K.) and measuring absorbance at 540 nm in a spectrophotometer.

After 6 days of treatment with BIM-23268C at 3 mg/kg, twice a day by subcutaneous injection, both plasma glycerol and triglycerides were significantly lowered, as exemplified by the samples taken at time 30 and 60 min. before the oral glucose challenge. The administration of an oral glucose challenge had no significant effect on plasma lipids. The BIM-23268C treated group showed significantly lower plasma glycerol and triglycerides through the 2-hour test period. The results suggested that BIM-23268C, following a 6-day treatment period at the prescribed dose was effective in reducing hypertriglyceridemia.

Measure of Efficacy in Patient

The effect of the somatostatin agonist will be assessed for a reduction in total cholesterol, total triglycerides, and total LDL cholesterol (e.g., as described in Dubrey, S. W., et al., Diabetes 43:831–835 (1994). The long term effect of the drug is examined by the change in coronary artery disease (Reviewed in Donahue, The Endocrinologist, 4:112–116 (1994).

Other Embodiments

The foregoing description has been limited to specific embodiments of this invention. It will be apparent, however, that variations and modifications may be made to the invention, with the attainment of some or all of the advantages of the invention. Such embodiments are also within the scope of the following claims.

The invention claimed is:

1. A pharmaceutical composition for the treatment of hyperlipidemia in a patient in need thereof, comprising a therapeutically effective amount of an agonist selective for the somatostatin type-5 receptor and having a higher binding affinity for the somatostatin type-5 receptor than for either the somatostatin type-1, type-2, type-3 or type-4 receptor and a binding affinity (Ki) of less than 5 nM for the somatostatin type-5 receptor, wherein said agonist is selected from the group consisting of H-Cys-Phe-Phe-D-Trp-Lys-Thr-Phe-Cys-NH$_2$; H-Cys-Phe-Phe-D-Trp-Lys-Ser-Phe-Cys-NH$_2$; H-Cys-Phe-Tyr-D-Trp-Lys-Thr-Phe-Cys-NH$_2$; H-Cys-Phe-Tyr(I)-D-Trp-Lys-Thr-Phe-Cys-NH$_2$; and

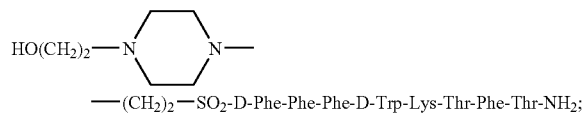

and wherein said therapeutically effective amount is an amount that is effective for the treatment of hyperlipidemia in said patient.

2. A pharmaceutical composition according to claim 1, wherein said agonist selective for the somatostatin type-5 receptor and having a higher binding affinity for the somatostatin type-5 receptor than for either the somatostatin type-1, type-2, type-3 or type-4 receptor has a Ki of less than 2 nM for the somatostatin type-5 receptor.

3. A pharmaceutical composition according to claim 1, wherein said agonist selective for the somatostatin type-5 receptor and having a higher binding affinity for the somatostatin type-5 receptor than for either the somatostatin type-1, type-2, type-3 or type-4 receptor has a Ki for the type-5 somatostatin receptor that is at least 10 times less than its Ki for the somatostatin type-2 receptor.

4. A pharmaceutical composition for lowering the amount of triacylglycerols in the blood of a patient in need of such lowering, comprising a therapeutically effective amount of an agonist selective for the somatostatin type-5 receptor and having a higher binding affinity for the somatostatin type-5 receptor than for either the somatostatin type-1, type-2, type-3 or type-4 receptor and a binding affinity (Ki) of less than 5 nM for the somatostatin type-5 receptor, wherein said agonist is selected from the group consisting of H-Cys-Phe-Phe-D-Trp-Lys-Thr-Phe-Cys-NH$_2$; H-Cys-Phe-Phe-D-Trp-Lys-Ser-Phe-Cys-NH$_2$; H-Cys-Phe-Tyr-D-Trp-Lys-Thr-Phe-Cys-NH$_2$; H-Cys-Phe-Tyr(I)-D-Trp-Lys-Thr-Phe-Cys-NH$_2$; and

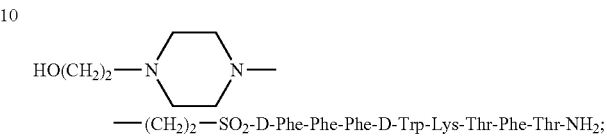

and wherein said therapeutically effective amount is an amount that is effective for lowering the amount of triacylglycerols in the blood of said patient.

5. A pharmaceutical composition according to claim 4, wherein said agonist selective for the somatostatin type-5 receptor and having a higher binding affinity for the somatostatin type-5 receptor than for either the somatostatin type-1, type-2, type-3 or type-4 receptor has a Ki of less than 2 nM for the somatostatin type-5 receptor.

6. A pharmaceutical composition according to claim 4, wherein said agonist selective for the somatostatin type-5 receptor and having a higher binding affinity for the somatostatin type-5 receptor than for either the somatostatin type-1, type-2, type-3 or type-4 receptor has a Ki for the type-5 somatostatin receptor that is at least 10 times less than its Ki for the somatostatin type-2 receptor.

7. A pharmaceutical composition for lowering the amount of glycerol in the blood of a patient in need of such lowering, comprising a therapeutically effective amount of an agonist selective for the somatostatin type-5 receptor and having a higher binding affinity for the somatostatin type-5 receptor than for either the somatostatin type-1, type-2, type-3 or type-4 receptor and a binding affinity (Ki) of less than 5 nM for the somatostatin type-5 receptor, wherein said agonist is selected from the group consisting of H-Cys-Phe-Phe-D-Trp-Lys-Thr-Phe-Cys-NH$_2$; H-Cys-Phe-Phe-D-Trp-Lys-Ser-Phe-Cys-NH$_2$; H-Cys-Phe-Tyr-D-Trp-Lys-Thr-Phe-Cys-NH$_2$; H-Cys-Phe-Tyr(I)-D-Trp-Lys-Thr-Phe-Cys-NH$_2$; and

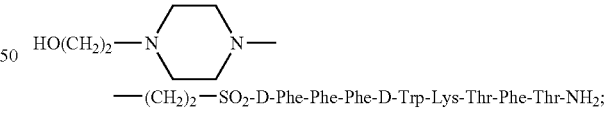

and wherein said therapeutically effective amount is an amount that is effective for lowering the amount of glycerol in the blood of said patient.

8. A pharmaceutical composition according to claim 7, wherein said agonist selective for the somatostatin type-5 receptor and having a higher binding affinity for the somatostatin type-5 receptor than for either the somatostatin type-1, type-2, type-3 or type-4 receptor has a Ki of less than 2 nM for the somatostatin type-5 receptor.

9. A pharmaceutical composition according to claim 7, wherein said agonist selective for the somatostatin type-5 receptor and having a higher binding affinity for the somatostatin type-5 receptor than for either the somatostatin type-1, type-2, type-3 or type-4 receptor has a Ki for the type-5 somatostatin receptor that is at least 10 times less than its Ki for the somatostatin type-2 receptor.

10. A pharmaceutical composition for lowering the amount of cholesterol in the blood of a patient in need of such lowering, comprising a therapeutically effective amount of an agonist selective for the somatostatin type-5 receptor and having a higher binding affinity for the somatostatin type-5 receptor than for either the somatostatin type-1, type-2, type-3 or type-4 receptor and a binding affinity (Ki) of less than 5 nM for the somatostatin type-5 receptor, wherein said agonist is selected from the group consisting of H-Cys-Phe-Phe-D-Trp-Lys-Thr-Phe-Cys-NH$_2$; H-Cys-Phe-Phe-D-Trp-Lys-Ser-Phe-Cys-NH$_2$; H-Cys-Phe-Tyr-D-Trp-Lys-Thr-Phe-Cys-NH$_2$; H-Cys-Phe-Tyr(I)-D-Trp-Lys-Thr-Phe-Cys-NH$_2$; and

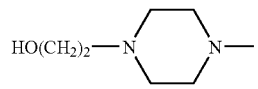

-continued

—(CH$_2$)$_2$—SO$_2$-D-Phe-Phe-Phe-D-Trp-Lys-Thr-Phe-Thr-NH$_2$;

and wherein said therapeutically effective amount is an amount that is effective for lowering the amount of cholesterol in the blood of said patient.

11. A pharmaceutical composition according to claim 10, wherein said agonist selective for the somatostatin type-5 receptor and having a higher binding affinity for the somatostatin type-5 receptor than for either the somatostatin type-1, type-2, type-3 or type-4 receptor has a Ki of less than 2 nM for the somatostatin type-5 receptor.

12. A pharmaceutical composition according to claim 10, wherein said agonist selective for the somatostatin type-5 receptor and having a higher binding affinity for the somatostatin type-5 receptor than for either the somatostatin type-1, type-2, type-3 or type-4 receptor has a Ki for the type-5 somatostatin receptor that is at least 10 times less than its Ki for the somatostatin type-2 receptor.

* * * * *